United States Patent [19]

Rom et al.

[11] Patent Number: 5,336,193
[45] Date of Patent: Aug. 9, 1994

[54] APPARATUS FOR SANITARY REMOVAL OF INDWELLING TUBES

[75] Inventors: Paul F. Rom, Kentwood; Roderick E. Briscoe, Rockford; Christopher R. Williams, Grand Rapids, all of Mich.

[73] Assignee: DLP, Inc., Grand Rapids, Mich.

[21] Appl. No.: 81,559

[22] Filed: Jun. 22, 1993

[51] Int. Cl.⁵ .......................................... A61M 25/00
[52] U.S. Cl. ................... 604/171; 604/263; 206/364
[58] Field of Search ............ 604/163, 171, 172, 263; 206/364, 365, 438, 69, 306, 210; 128/856

[56] References Cited

U.S. PATENT DOCUMENTS

| | | |
|---|---|---|
| 1,120,549 | 12/1914 | Schellberg . |
| 1,196,250 | 8/1916 | Kuhn . |
| 1,351,917 | 9/1920 | Kuhn . |
| 2,856,932 | 10/1958 | Griffitts . |
| 3,244,169 | 4/1966 | Baxter . |
| 3,709,223 | 1/1973 | Macalalad et al. . |
| 3,726,283 | 4/1973 | Dye et al. . |
| 3,742,960 | 7/1973 | Dye et al. . |
| 3,766,915 | 10/1973 | Rychlik . |
| 3,825,001 | 7/1974 | Bennet et al. . |
| 3,894,540 | 7/1975 | Bonner, Jr. . |
| 3,934,721 | 1/1976 | Juster et al. . |
| 3,967,728 | 7/1976 | Gordon et al. . |
| 4,140,127 | 2/1979 | Cianci et al. . |
| 4,227,533 | 10/1980 | Godfrey . |
| 4,230,115 | 10/1980 | Walz, Jr. et al. . |
| 4,392,853 | 7/1983 | Muto . |
| 4,691,702 | 9/1987 | Chantzis ........................ 604/163 |
| 4,767,409 | 8/1988 | Brooks .......................... 604/163 |
| 4,772,275 | 9/1988 | Erlich . |
| 4,790,834 | 12/1988 | Austin . |
| 4,878,762 | 11/1989 | Uddo, Jr. et al. . |
| 4,887,615 | 12/1989 | Taylor . |
| 5,181,913 | 1/1993 | Erlich . |

Primary Examiner—John D. Yasko
Assistant Examiner—Anthony Gutowski
Attorney, Agent, or Firm—Harris Beach & Wilcox

[57] ABSTRACT

There is disclosed an apparatus comprising a hub that includes an annular container disposed about a central aperture for receiving an exterior portion of an indwelling tube therethrough to engage a bottom portion of the container in sealing contact with the implantation site. An extensible impervious membrane is folded within the container and is in sealing contact therewith, the membrane being arranged to form an open sleeve for receiving the tube and being coextensible therewith during withdrawal of the tube. A tie is provided to seal the sleeve about the exterior wall of tube, leaving the free end of the tube accessible to the operator. The indwelling tube can then be withdrawn through the central aperture into the coextending closed sleeve. A plastic film that adheres to the bottom portion of the container is provided for closing the central aperture to enclose the removed tube in the sleeve.

9 Claims, 2 Drawing Sheets

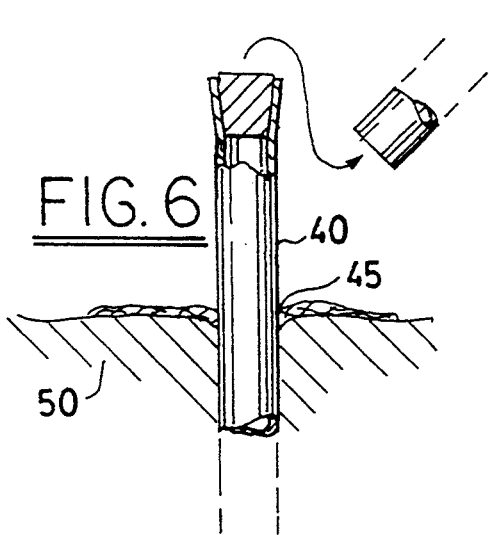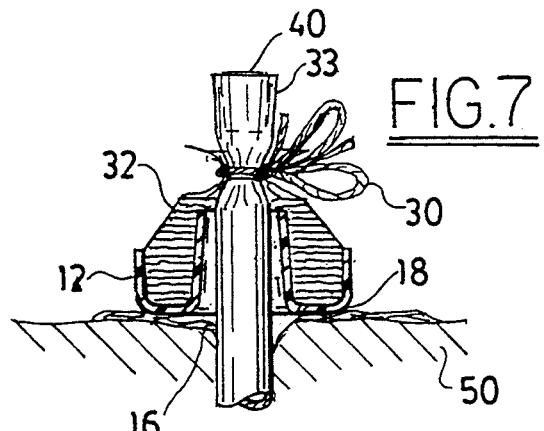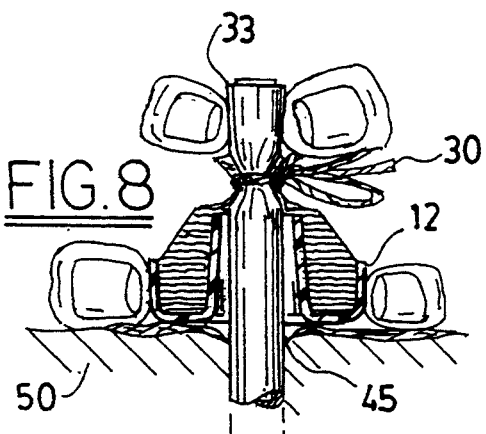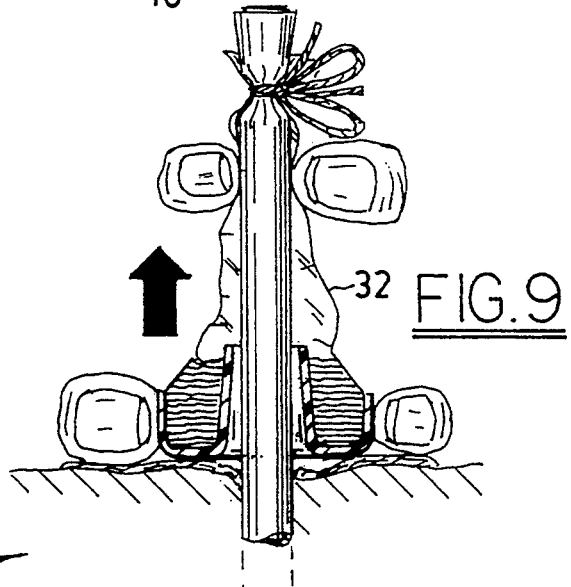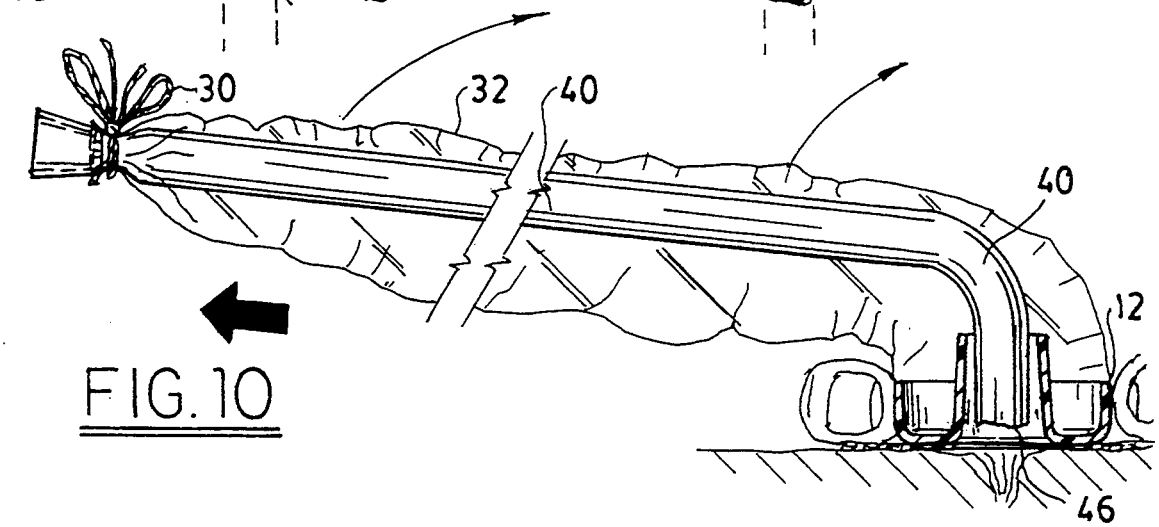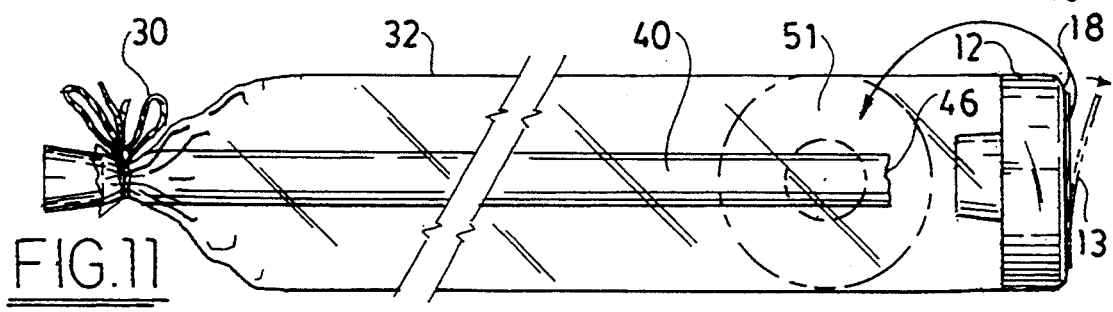

APPARATUS FOR SANITARY REMOVAL OF INDWELLING TUBES

BACKGROUND OF THE INVENTION

1. Field of the Invention

This invention relates to the sanitary removal of drains and tubes which are indwelling in the body of a patient. More particularly this invention relates to an apparatus for isolating a body drain and its site of insertion while removing the drain, in order to protect the health care worker and the environment.

2. Description of the Prior Art

In recent years recognition has come that blood and body fluids, which carry pathogens such as bacteria and the hepatitis B and human immunodeficiency viruses, represent a serious threat to health care workers, and a general biohazard in the environment. Safety practices and health care regulations have accordingly been strengthened, and it now is standard practice for health care workers to employ universal precautions when working with potentially infectious patients, their blood, secretions, and other body fluids.

Indwelling tubes such as chest tubes, endotracheal tubes, nasogastric tubes, and various catheters are commonplace in modern patient care. These tubes are necessarily in contact with potentially hazardous blood and body fluids. When they are removed from the patient there is risk of contamination by direct contact with the exposed tube. Further biohazard is risked in consequence of blood and body fluids dripping from the tube, or flowing from a body orifice or an implantation site during its removal. Some tubes are notoriously difficult to control during removal, which can lead to spattering and spraying of infectious body fluids in the patient area, and even the formation of aerosols which pose a serious health risk to those nearby.

A device for removing monitoring tubes is disclosed in Uddo Jr. et al, U.S. Pat. No. 4,878,762 in which a tube to be removed is received into the open mouth of a canister, and into the blind tip of a fully retracted sheath bonded thereto, after which the tube is pulled out of the patient, and the sheath drawn into full extension therewith. The canister is then capped, enclosing the tube for sanitary disposal. This system does not permit the tube to remain attached to a suction or drain hose during removal, as may be desirable in certain applications, because the tube's free end is immediately isolated prior to delivery from the patient.

SUMMARY OF THE INVENTION

It is therefore a primary object of the present invention to provide an improved apparatus for removing an indwelling tube from a patient while preventing contact between the tube, the environment, and persons in the vicinity.

It is another object of the invention to provide a sealable unit for the sanitary disposal of a removed indwelling tube therein.

It is a further object of the invention to remove an indwelling tube in an aseptic manner while isolating the tube and the implantation site from an environment thereabout.

It is yet another object to prevent contamination of the environment during the operation of removing an indwelling tube from a patient.

These and other objects of the present invention are attained by an apparatus comprising a container having an aperture that can receive an exterior portion of the indwelling tube therethrough to engage a bottom portion of the container in sealing contact about the implantation site. An extensible impervious membrane is folded within the container and is in sealing contact therewith, the membrane being arranged to form an open sleeve for receiving the tube and being coextensible therewith during withdrawal of the tube. A tie is provided to seal the sleeve about the exterior wall of tube, leaving the free end of the tube accessible to the operator. The indwelling tube can then be withdrawn through the central aperture into the coextending closed sleeve.

In accordance with one aspect of the invention a membrane such as a plastic film that adheres to the bottom portion of the container is provided for closing the central aperture to enclose the removed tube in the sleeve.

In accordance with another aspect of the invention the container is annular, and is included in a hub having a central aperture.

BRIEF DESCRIPTION OF THE DRAWING

For a better understanding of these and other objects of the present invention, reference is made to the detailed description of the invention which is to be read in conjunction with the following drawings, wherein:

FIGS. 6-11 illustrate the process of removing a tube or drain utilizing the device of FIG. 1.

DESCRIPTION OF THE PREFERRED EMBODIMENT

Figure 1:
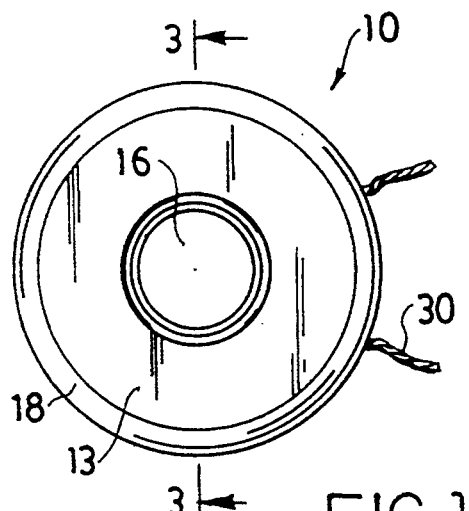
FIG. 1 is a bottom plan view of a tube and drain removal device in accordance with the invention.
Figure 2:
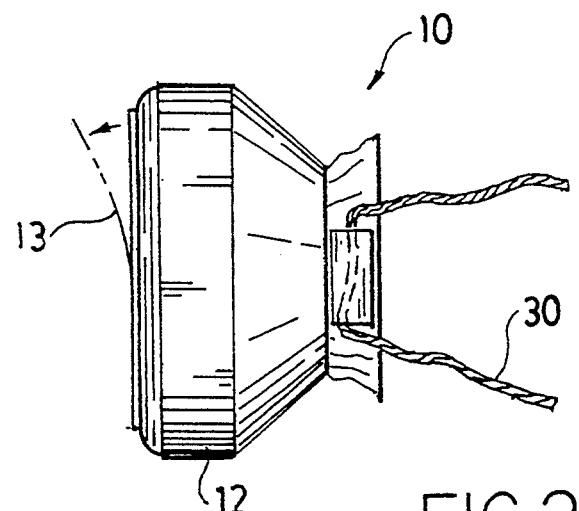
FIG. 2 is a side elevation of the device shown in FIG. 1.

In FIGS. 1-5 there is shown a preferred embodiment of a drain removal device 10 in accordance with the invention. A hub 12, fabricated by plastic injection molding, or other suitable methods known to the art, has a central aperture or passage 16, dimensioned to allow an indwelling tube which is being removed to pass therethrough. The hub has an annular container portion 14, defined by side wall 17, bottom 18, and medial wall 19. The bottom portion of passage 16 is sealed by a plastic film 13, having a suitable adhesive, such as an inherently tacky microspheric glue applied thereon. The film 13 thus adheres to bottom 18, and can be stripped off and reapplied as required.

Figure 3:
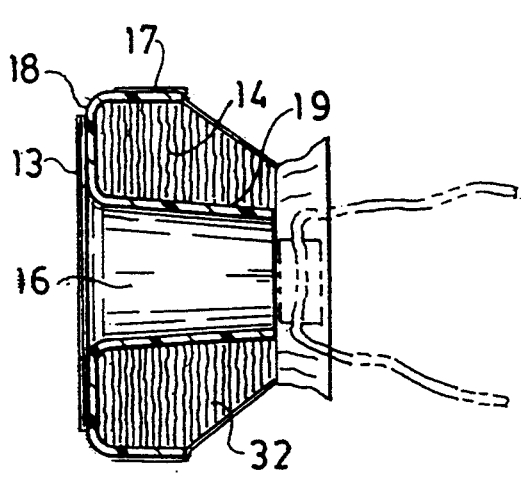
FIG. 3 is a sectional view through line 3—3 of FIG. 1.
Figure 4:
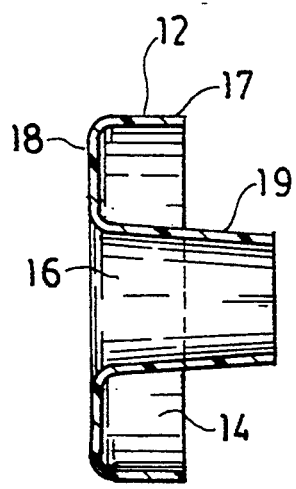
FIG. 4 is a sectional view through line 3—3 of FIG. 1 with the flexible sleeve removed.
Figure 5:
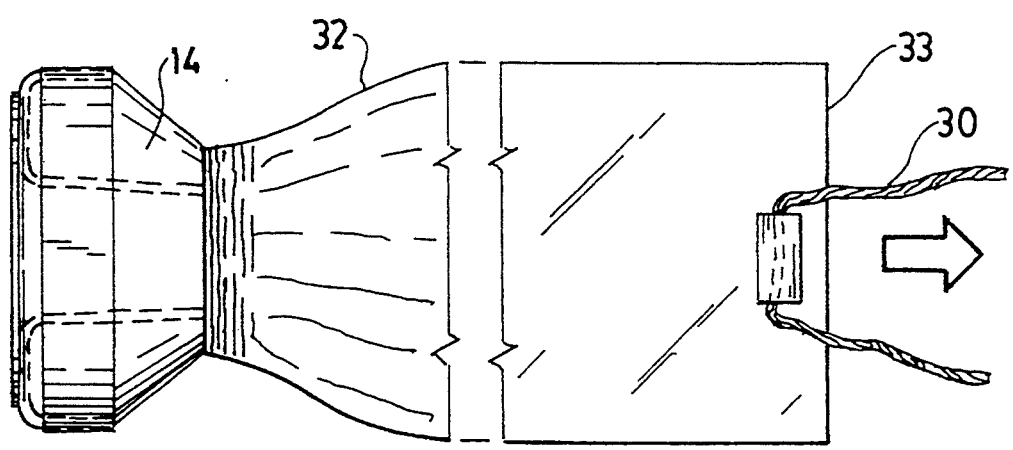
FIG. 5 is a side elevation of the device shown in FIG. 1 with the flexible sleeve extended.

As best shown in FIGS. 3 and 5, container portion 14 is occupied by a sleeve 32 of fan-folded flexible plastic material such as polyethylene sheet. One end of sleeve 32 is sealably bonded to container 14. Sleeve 32 can be unfolded to extend from hub 12 to form a sleeve as shown in FIG. 1, having a free end 33. A tie 30 is provided near the free end 33 of sleeve 32, and when it is pulled tight a sealed container, whose contents are isolated from the environment, is defined by sleeve 32, container portion 14, and film 13. In assembly, the folded sleeve 32 can be retained within container portion 14 by a shrink wrapped film (not shown).

To understand how to use device 10 reference may be had to FIGS. 6–11, in which there is shown an indwelling tube 40 which has been implanted through site 45 of the body of a patient 50, and is required to be removed in a sanitary manner. First film 13 is detached from the hub 12 to provide entry to passage 16. Then the free end 33 of sleeve 32 is mobilized and extended upward a short distance. With the bottom 18 of hub 12 directed toward the body of the patient 50, the free end of indwelling tube 40 is received through the central passage 16 as shown in FIG. 7. As the bottom 18 of the hub 12 is brought into contact with the body surface of the patient 50 around the tube 40 and the implantation site 45, the exterior portion of the tube 40 passes through the hub, the free end of the tube coming substantially into alignment with the free end 33 of the partially extended sleeve 32.

Now the tie 30 is tightened and knotted to secure tube 40 and sleeve 32 together, so that the indwelling tube 40 cannot readily slip off during withdrawal.

It will be appreciated that the free end of tube 40 remains accessible, and it may be connected by a suitable adapter to an external drainage tube (not shown), so that its contents can be evacuated during its withdrawal.

With the hub 12 maintained in contact with the patient 50 by the operator, the sleeve 32 is grasped near its free end 31, grasping pressure thus being applied to the end portion of the tube 40 contained therewithin. Traction is thereupon exerted to extend the sleeve 32 (see FIG. 9) and withdraw the tube 40 therewith from the patient 50, the tube 40 being contained within a pouch defined by the extending sleeve 32, now placed in sealing contact with the exterior of tube 40 by tie 30.

As shown in FIGS. 10 and 11 the tube 40 is fully withdrawn from the patient 50, and its distal end 46 has entirely passed through the hub 12, so that the tube is substantially contained within the sleeve 32. Film 13, which may temporarily be retained by suitably prepared pad 51 on the exterior wall of the sleeve 32, is now reapplied against the bottom 18 to close off passage 16 and completely encase the tube 40.

It will be appreciated that while the tube is being withdrawn into the sleeve, the exterior portions of the tube 40 and the surgical implantation site 45 are enclosed within a sealed compartment and completely isolated from the environment. When the device 10 with the tube 40 contained within are removed from the patient 50 for disposal, it may be expedient to place a gauze or the like (not shown) over the surgical site 45.

While this invention has been explained with reference to the structure disclosed herein, it is not confined to the details set forth and this application is intended to cover any modifications and changes as may come within the scope of the following claims:

What is claimed is:

1. An apparatus for the sanitary removal of an indwelling tube from an implantation site of a patient while isolating the tube and the implantation site from an environment thereabout, comprising:
   a container having an aperture that can receive an exterior portion of the indwelling tube therethrough to engage a bottom portion of said container in sealing contact with the patient about the implantation site;
   an extensible impervious membrane folded within said container and being in sealing contact therewith, said membrane being arranged to form an open sleeve for receiving the tube and being coextensible therewith during withdrawal of the tube;
   means for placing said sleeve in sealing contact with the tube; and
   means for closing said aperture to enclose the removed tube in said sleeve;
   whereby the tube can be withdrawn through said aperture into said coextending sleeve, and the free end of the tube remains accessible to an operator as the tube is withdrawn.

2. The apparatus of claim 1, wherein said means for closing comprises a plastic film that adheres to said bottom portion of said container.

3. The apparatus of claim 1, wherein said means for placing comprises a tie attached proximate a free end of said sleeve.

4. An apparatus for the sanitary removal of an indwelling tube from an implantation site of a patient, while isolating the tube and the implantation site from an environment thereabout, comprising:
   an annular container having an aperture that can receive an exterior portion of the indwelling tube therethrough to engage a bottom portion of said container in sealing contact with the patient about the implantation site;
   an extensible impervious membrane disposed in said container and being in sealing contact therewith, said membrane being arranged to form an open sleeve about the tube;
   a tie attached proximate a free end of said sleeve to enclose a portion of the tube therein and for excluding a free end of the tube from said enclosed portion, so that the free end of the tube is accessible to an operator; and
   means for closing said aperture to enclose the removed tube in said sleeve;
   whereby the tube can be withdrawn through said aperture into said sleeve, and the tube and the implantation site are isolated from an environment when the tube is withdrawn.

5. The apparatus of claim 4, wherein said means for closing comprises a plastic film that adheres to said bottom portion of said container.

6. A method for the sanitary removal of an indwelling tube from an implantation site in a patient, comprising the steps of:
   folding a flexible impervious membrane into an annular container in sealing contact therewith;
   passing an exterior portion of the indwelling tube through an aperture of said annular container to engage a bottom portion of said container with the implantation site;
   sealing a free end of said membrane about an exterior wall of the tube proximate an end thereof to enclose a portion of the tube therein, a free end of the tube remaining accessible to an operator; and
   simultaneously withdrawing the tube and coextending said membrane to form a sleeve thereabout; and closing said aperture to enclose said withdrawn tube.

7. The method of claim 6, wherein said step of sealing said free end of said membrane is performed with a tie.

8. The method of claim 6, wherein said step of closing said aperture is performed with an adherent plastic film.

9. The method of claim 6, further comprising the step of connecting said free end of the indwelling tube to an external drainage tube after said step of passing said exterior portion of the indwelling tube through said aperture.

* * * * *